United States Patent [19]

White

[11] 4,034,190
[45] July 5, 1977

[54] METHOD AND APPARATUS FOR REMOTE SALINITY SENSING

[75] Inventor: Peter G. White, Palos Verdes Peninsula, Calif.

[73] Assignee: TRW Inc., Redondo Beach, Calif.

[22] Filed: Mar. 15, 1974

[21] Appl. No.: 451,391

[52] U.S. Cl. .............................. 235/151.3; 340/236; 356/114
[51] Int. Cl.² ............................................ G01V 1/28
[58] Field of Search ......... 235/151.3, 92 V, 92 DT; 356/128, 107, 114, 118; 340/236; 324/30 R

[56] References Cited

UNITED STATES PATENTS

| 3,131,346 | 4/1964 | Parke | 340/236 |
| 3,263,224 | 7/1966 | Berman et al. | 340/236 |
| 3,717,753 | 2/1973 | Thomas | 235/151.3 |

OTHER PUBLICATIONS

"Measurement of the Index of Refraction of Some Molten Ionic Salts", *The Review of Scientific Instruments*, Jules Marcoux, vol. 42, No. 5, May 1971, pp. 600–602.

*Primary Examiner*—Felix D. Gruber
*Assistant Examiner*—Errol A. Krass
*Attorney, Agent, or Firm*—John J. Connors; Edwin A. Oser; Stephen J. Koundakjian

[57] ABSTRACT

Disclosed is a method and apparatus for remote sensing of the salinity of large bodies of water.

A sequence of intensity values is obtained for the horizontally and vertically polarized components of sunlight specularly reflected as a solar glitter pattern at successive points on the surface of the body of water. For readings corresponding to each pair of points, the fractional change of horizontal and vertical component intensity between the points is computed, as in the ratio of the fractional change in the vertical component to the fractional change in the horizontal component. If the ratio is sufficiently near a theoretical value, dependent on the solar zenith angle, to indicate that the corresponding intensity changes were actually caused by a change in salinity, the salinity change is calculated using formulae derived from the Fresnel equations.

21 Claims, 7 Drawing Figures

METHOD AND APPARATUS FOR REMOTE SALINITY SENSING

BACKGROUND OF THE INVENTION

A. Field of the Invention

This invention relates to methods and apparatus for the remote measurement of the salinity of large bodies of water.

B. Description of Prior Art

Salinity is typically measured by laboratory analysis of an actual sample of water from the body under investigation. For example, the water may be evaporated and the salt residue weighed. As an alternative method, the water may be titrated with silver nitrate to precipitate silver chloride (or metallic silver, upon exposure to light) which may be filtered out and weighed.

In many applications, however, it is not possible to take a sufficient number of samples of the water for adequate testing and analysis. The commonest example of such a situation is where a large body, such as a gulf, is subjected to salinity mapping. In situations such as this, a remote salinity sensing method and apparatus would be quite useful.

There exists a microwave remote salinity analysis technique. Here, thermal emissions from the body of water are remotely sensed in the microwave band from a satellite or high-flying aircraft. Mathematical methods exist for the computation of salinity if the water temperature and surface roughness are known.

However, numerous difficulties have been encountered is using this prior art method. For example, since thermal emissions form the basis for the measurement, the temperature of the water is quite critical and must be measured with great accuracy if usable results are to be obtained from the salinity calculations. Furthermore, since a microwave source emits at a much lower frequency than a visible light source, the microwave antenna must be rather large to avoid signal-to-noise problems.

SUMMARY OF THE INVENTION

Accordingly, it is an object of the present invention to provide a method and apparatus for remote salinity measurement utilizing reflected light which may be in the visible region.

Briefly, in the method of the present invention, the solar glitter pattern from a body of water is continuously sensed as the sensor moves across the surface, perhaps at satellite height. Since the light will, to a large degree, be vertically and horizontally polarized upon reflection from the surface, the light received by the sensor is polarization analyzed along each plane, and the intensity of both polarized components is detected. For each intensity reading of the vertical components, the fractional change of intensity over all (or a large fixed number of) previous such readings is calculated. The same is done with the intensity readings of the horizontally polarized component. The ratio of each corresponding set of vertical to horizontal changes is calculated. Depending on the solar zenith angle (i.e. 90° minus the elevation angle from the horizon), these ratios will, by comparison with theoretical values, indicate which of the intensity changes have resulted from a change in salinity, as opposed to other factors, such as sea state. For each intensity change determined to result from a salinity change, the actual change in salinity is calculated, using formulae derived from the Fresnel equations.

The apparatus comprises sensor means to acquire corresponding intensity values for the horizontally and vertically polarized light from the solar glitter pattern. These values are analyzed by means for calculation in accordance with the above-described method.

DETAILED DESCRIPTION OF THE PREFERRED EMBODIMENT

The measurement of ocean salinity by means of the present invention is based on the fact that the index of refraction of ocean water varies with salinity in a linear fashion, according to the relationship:

$$n = aS + b, \quad (1)$$

where $n$ = the index of refraction $S$ = salinity; and $a$ and $b$ are constants.

The particular effect of this relationship which is of interest here is the fact that, to a large degree, the intensities of the horizontally and vertically polarized components of sunlight reflected from the sea surface depend, in a known manner, on the index of refraction, and, thus, the salinity of the water.

Figure 4:
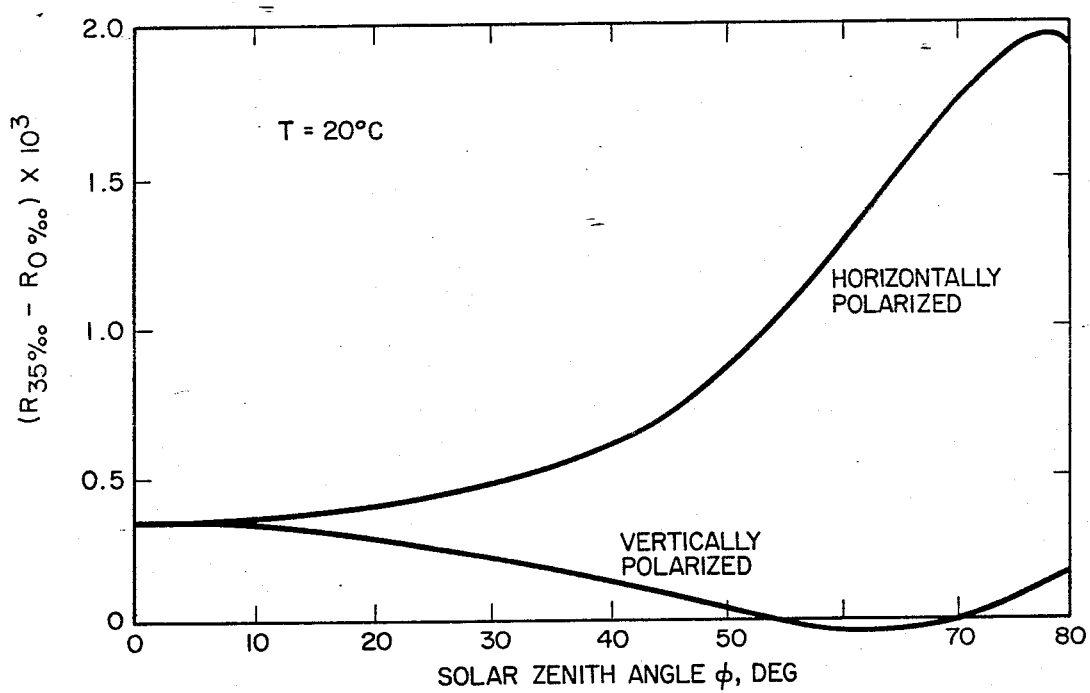
FIG. 4 is a pair of curves wherein the abscissa represents the solar zenith angle; one ordinant represents the difference in reflectance, between water having 35 parts per thousand salinity ($R_{35‰}$) and water having no salinity ($R_{0‰}$), of the horizontally polarized component of reflected light; and the other ordinant represents the same for the vertically polarized component.

This is shown empirically in FIG. 4. Here, the upper curve represents the difference in reflectivity $\Delta R_H$ of the horizontally polarized component of reflected light between water of 35 ‰ (parts per thousand) salt and fresh water. The lower curve shows the same difference $\Delta R_V$ for the vertically polarized component.

The analytic relationships are summarized in the Fresnel equations:

$$R_V = \frac{\tan^2 (i-r)}{\tan^2 (i+r)} \quad (2)$$

$$R_H = \frac{\sin^2 (i-r)}{\sin^2 (i+r)}; \text{ and Snell's law:} \quad (3)$$

$$r = \sin^{-1}\left(\frac{\sin i}{n}\right), \text{ where:} \quad (4)$$

$i$ = incidence angle of the light impinging on the water surface from above = the solar zenith angle, $\phi$, if the specularly reflected glitter pattern is viewed from the side opposite the sun;

$r$ = the angle of refraction;

$R_V$ = the reflectance of the vertically polarized component of the light specularly reflected from the ocean surface. It is proportional to the intensity of the vertically polarized light detected by remotely sensing the glitter pattern; and $R_H$ = the reflectance of the horizontally polarized component of the light specularly reflected from the ocean surface. It is also proportional to the intensity of the horizontally polarized light detected by remotely sensing the glitter pattern.

Thus, as a first approximation, one may determine the salinity of ocean water by measuring: (a) the intensities of the horizontally and vertically polarized light reflected from the surface, and (b) the solar zenith angle.

However, while the index of refraction of the water does not vary with the surface roughness of the water (normally caused by wind), the actual intensity of specularly reflected polarized light remotely measured along any sight line does vary with the surface roughness. This is because, while light can be specularly reflected from a relatively flat surface with a minimum of intensity loss, a choppy surface will tend to scatter the light, and only a portion will be specularly reflected.

Atmospheric effects, such as scattering of light from dust particles or water droplets can also have a pronounced effect on otherwise "pure" remote specular reflection intensity readings, particularly if the actual reflected intensity is diminished by surface roughness caused by wind or similar agents.

Accordingly, some method must be provided for determining whether particular remotely sensed intensity readings provide valid data from which the salinity may be calculated.

I have discovered such a method.

Differentiating the Fresnel equations, (2) and (3), with respect to the index of refraction, $n$, after substituting, from Snell's Law [equation (4)], the value of $r$ we see that:

$$\frac{dR_V}{dn} = 4R_V \sin i \cdot \tan i \cdot \frac{n}{K} \left( \frac{1}{K^2 \tan^2 i - \sin^2 i} + \frac{1}{K^2 - \sin^2 i \tan^2 i} \right),$$

and $$\frac{dR_H}{dn} = 4R_H \cos i \cdot \frac{n}{K} \left( \frac{1}{K^2 - \cos i} \right), \text{ where } K^2 = n^2 - \sin^2 i$$

From these relationships, it can be seen that:

$$\frac{\frac{dR_V}{R_V}}{\frac{dR_H}{R_H}} = \frac{n^2 - 1}{\frac{n^2}{\tan^2 i} - 1} + 1$$

Assuming that, for practical purposes, the total derivative is equal to the ratio of finite differences, i.e.:

$$\frac{dR_V}{dR_H} = \frac{\Delta R_V}{\Delta R_H},$$

it follows that:

$$\frac{\frac{\Delta R_V}{R_V}}{\frac{\Delta R_H}{R_H}} = \frac{n^2 - 1}{\frac{n^2}{\tan^2 i} - 1} + 1 \tag{5}$$

We see, therefore, that there is a definite theoretical relationship between the fractional change in reflectance for the vertically polarized component of reflected light divided by the corresponding fractional change in the horizontally polarized component, on the one hand, and the index of refraction, $n$, and the incidence angle, , on the other hand. Rewriting equation (5) as:

$$\frac{\frac{\Delta R_V}{R_V}}{\frac{\Delta R_H}{R_H}} = \tan^2 i \left( \frac{n^2 - 1}{n^2 - \tan^2 i} \right) + 1, \tag{5a}$$

we can see that the theoretical relation depends primarily on the light incidence angle, and only weakly on the index of refraction of the initial (or final) water sample observed, since the index of refraction, $n$, of the water can vary only within a rather small range, while $\tan^2 i$ can vary from 0 to infinity.

Because of this weak dependence of the right-hand quantity in equations (5) and (5a) on the index of refraction, we may equate it to a theoretical reference factor:

$$L'(i) = \frac{\frac{\Delta R_V}{R_V}}{\frac{\Delta R_H}{R_H}}$$

Since, for specular reflections, the incidence angle, $i$, in equations (5) and (5a) is equal to the solar zenith angle, $\phi$, we may assume that, for practical purposes, $L'$ depends on $\phi$, i.e., $$L'(\phi) = \tan^2 \phi \left( \frac{n^2 - 1}{n^2 - \tan^2 \phi} \right) + 1 \tag{6}$$

Figure 5:
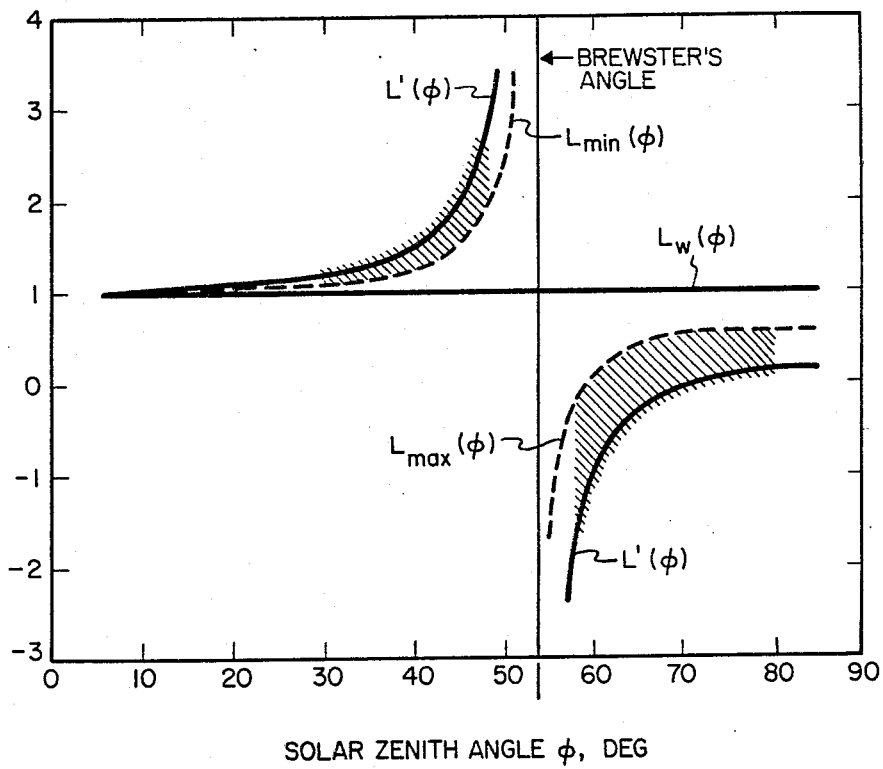
FIG. 5 is a graph showing relationships existing between values of the solar zenith angle, $\phi$, and the various values of the reference factor, L, as more fully described below.

A typical $L'(\phi)$ versus $\phi$ curve is shown in FIG. 5.

The actual reflectance of the vertically and horizontally polarized components cannot be accurately measured remotely. What can be measured as the *apparent* intensity of these components sensed at the remote location. I.e., we cannot remotely measure:

$$L'(\phi) = \frac{\frac{\Delta R_V}{R_V}}{\frac{\Delta R_H}{R_H}}.$$

but we can measure $$L(\phi) = \frac{\frac{\Delta I_V}{I_V}}{\frac{\Delta I_H}{I_H}}, \text{ where:}$$

where:
$L(\phi)$ = the empirical reference factor;
$I_V$ = the "current" ($m^{th}$) measured intensity of the vertically polarized component of the reflected light;
$I_H$ = the "current" ($m^{th}$) measured intensity of the horizontally polarized component of the reflected light;
$\Delta I_V$ = the change in $I_V$ between the $m^{th}$ measurement and a previous $j^{th}$ measurement, i.e., $\Delta I_V = \Delta I_{V_{jm}}$; and
$\Delta I_H$ = the change in $I_H$ between the $j^{th}$ measurement and a previous $m^{th}$ measurement, i.e., $\Delta I_H = \Delta I_{H_{jm}}$.

Expressed slightly differently, then, the empirical reference factor, $$L_{jm} = \frac{\frac{I_{V_m} - I_{V_j}}{I_{V_m}}}{\frac{I_{H_m} - I_{H_j}}{I_{H_m}}} \quad (7)$$

It is this factor, $L_{jm}$, which permits a determination of whether or not a particular pair of vertical polarization intensity measurements and the corresponding pair of horizontal polarization intensity measurements may be used to reliably compute a value for the salinity at the location of the current ($m^{th}$) measurement, or, more precisely stated, the change in the salinity between the $m^{th}$ and the previous ($j^{th}$) measurement points.

Specifically, I have discovered that where there is a change in surface condition between the $j^{th}$ and the $m^{th}$ measurement, which change will cause the intensity measurements to be unreliable, the value of the empirical reference factor, $L_{jm}$, will be very nearly that shown as $L_W(\phi)$ in FIG. 5. As shown in that curve, $L_2(\phi)$ equals 1.0 for all values of the solar zenith angle, $\phi$. On the other hand, the theoretical reference factor $L'(\phi)$ is considerably greater than 1.0 from about $\phi = 20°$ to about $\phi = 48°$, considerable less than 0.0 from about 58° to about 70°, and considerably less than the value of $L_W(\phi)$ beyond that angle.

Consequently, if the calculated value of the empirical reference factor $L_{jm}$ for a "set" of (i.e., the horizontally and corresponding vertically polarized component intensities from two points) measurements is reasonably near the theoretical value $L'(\phi)$ for the particular solar zenith angle, $\phi$, and the value of $\phi$ is within a certain range, one may be assured that that set of measurements will yield a reliable value for the calculated salinity change between the two points monitored. This value is calculated from equations (1), (3) and (4) by:

a. Assuming for each of the two ($j^{th}$ and $m^{th}$) measurement "pairs" (horizontally and vertically polarized component intensities) in the set, that:
$I_{H_j} = K_R H_j$ (i.e., that the transfer function, $K_R$, of the instrument is known from previous laboratory measurement);
$I_{H_m} = K_R H_m$ (same assumption);
$\phi_j = i_j = \phi_m = i_m$ (i.e., there is specular reflection, and the solar zenith angle changes only immaterially during an entire measurement sequence which will, typically, occupy only a few minutes at the most).

b. Calculating $r_j$ and $r_m$ by solving for r in equation (3), using, respectively, the $j^{th}$ and $m^{th}$ values of $I_H$ [equation (2) could be employed with values of $I_V$, but the computation proves to be simpler if equation (3) is used];

c. Calculating $n_j$ and $n_m$ from Snell's Law [equation (4)] by using the computed values of $r_j$ and $r_m$;

d. Calculating $S_j$ and $S_m$ from equation (1) (the constants will presumably have been calculated previously by direct salinity measurement or found from a published reference work); and, finally, e. Calculating $\Delta S_{jm}$ by subtracting $S_j$ from $S_m$.

Again, prior to calculating $\Delta S_{mj}$, it is necessary to determine that the calculated value will be reliable, i.e., that the corresponding values of $L_{jm}$ and $\phi$ are "proper." This is done by the following method:

We first define the following quantities:
$\phi_A$ = the smallest solar zenith angle from which reliable data may be obtained;
$\phi_B$ = the largest solar zenith angle below Brewster's angle from which reliable data may be obtained;
$\phi_C$ = the smallest solar zenith angle above Brewster's angle from which reliable data may be obtained;
$\phi_D$ = the largest solar zenith angle from which reliable data may be obtained; $L_{min}(\phi)$ = the lowest value of $L_{jm}$ which can be observed if a reliable value of $\Delta S_{jm}$ may be calculated, where $\phi_A \leq \phi \leq \phi_B$; and
$L_{max}(\phi)$ = the highest value of $L_{jm}$ which can be observed if a reliable value of $\Delta S_{jm}$ may be calculated, where $\phi_C \leq \phi \leq \phi_D$.

I have found that a reliable value of $\Delta S_{jm}$ may be calculated if either of the following conditions exists:

[CONDITION "A"]: $\phi_A \leq \phi \leq \phi_B$; and $$L_{jm} \geq L_{min}(\phi), \text{ where } \phi_A = 30°; \\ \phi_B = 48°; \text{ and}$$

$$L_{min}(\phi) = \frac{L'(\phi) - 1}{2}$$

or

[CONDITION "B"]: $\phi_C \leq \phi \leq \phi_D$; and $$L_{jm} \leq L_{max}(\phi), \text{ where } \phi_C = 58°; \\ \phi_D = 80°; \text{ and}$$

$$L_{max}(\phi) = \frac{1 + L'(\phi)}{2}$$

FIG. 5 shows the relationship between the various critical values of $\phi$ and the corresponding values of $L'(\phi)$, $L_W(\phi)$, $L_{min}(\phi)$ and $L_{max}(\phi)$, with the cross-hatched regions representing the range of preferred $L_{jm}$ and $\phi$ values. It will be noted that the cross-hatching extends beyond $L'(\phi)$, since I have observed that it is possible, under unusual atmospheric conditions, to obtain calculated values of $L_{jm}$ in the indicated extended range.

In essence, therefore, the remote salinity sensing method of the present invention comprises obtaining a number of pairs of corresponding values of intensity of the horizontally and vertically polarized components of reflected light, determining whether, within any data set (i.e., between any given two pairs), observed intensity changes were caused by a salinity change and, if so, utilizing the Fresnel equations to determine, ultimately, the change in salinity between the two points from which the two pairs of measurements were respectively taken.

Having described the method in general terms, it will now be described in detail in connection with a description of the preferred embodiment of the apparatus of the present invention.

The apparatus must provide means for separate intensity measurement of the horizontally and vertically polarized components of the reflected light beam.

Figure 1:
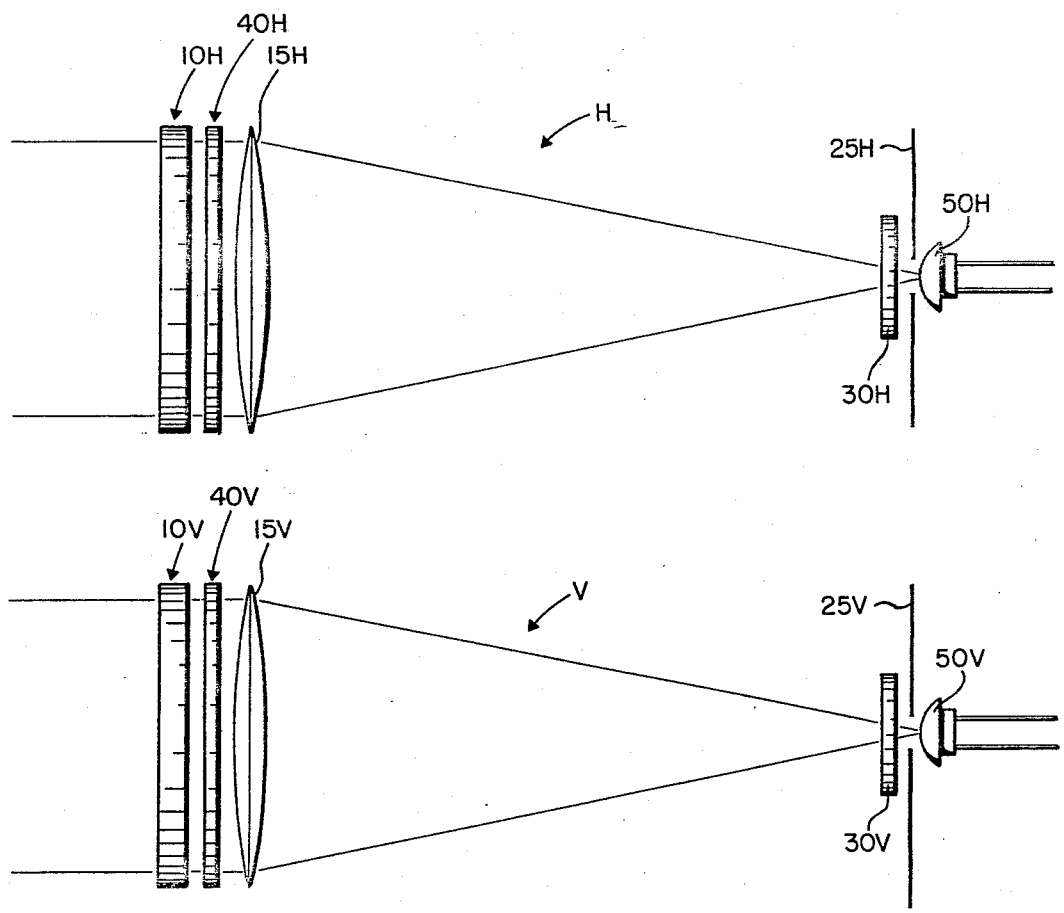
FIG. 1 is a schematic representation of the optical portion of the preferred embodiment of the apparatus of the present invention.

The simplest and preferred means for accomplishing this is illustrated in FIG. 1.

In the embodiment illustrated, a separate optical device is utilized for each component — each element of the device, H, utilized in measuring the intensity of the horizontally polarized component is shown with the index numerals having a suffix H, while the representation of the "vertical" device, V, utilizes V suffixes. As shown, the two devices are aligned with their optical axes parallel so that each device obtains its readings from the same remote location. In particular, a single housing may be utilized for the pair of optical devices. Such a housing is not illustrated, as it is conventional and forms no part of the invention.

The two devices are, of course, calibrated so that they will exhibit substantially identical sensitivity.

Referring now to FIG. 1, in the preferred embodiment of the apparatus of the present invention, light specularly reflected from the solar glitter pattern on the water surface is first reduced in intensity by neutral filters 10H, 10V. The purpose of this intensity reduction is to avoid saturation of the detectors by the high intensity reflected light beam.

Each of the objective lenses 15H, 15V focuses one of the reduced intensity beams onto a corresponding field stop aperture 25H, 25V. Intervening between each objective lens and the corresponding aperture is a narrow-band (approximately 150 angstroms) filter 30H, 30V. The purpose of this filter is to narrow the wavelength band of the transmitted beams and, thus, to avoid problems which might otherwise arise because of the dependency of the index of refraction of the water on the wavelength of the light impinging upon it and reflected from it.

A polarization analyzer, 40H, which is preferably an ordinary sheet polarizer with its polarization plane oriented horizontally with respect to the water surface being remotely sensed, intervenes between the neutral filter 10H and objective lens 15H. Likewise, a vertically oriented polarization analyzer 40V intervenes between the other neutral filter 10V and its corresponding objective lens 15V. The purpose of these analyzers is to divide the reflected light received by the salinity sensor into separate beams for separate detection of the intensity of the horizontally and vertically polarized components.

There are other means by which a pair of beams may be created for separate analysis.

For example, separate analysis of the intensity of the horizontally and vertically polarized components may be made in a single-barrelled instrument. This may be accomplished by placing a rotating analyzer in the path of the beam. As the analyzer's polarization plane rotates, it will alternately pass the horizontally polarized component and the vertically polarized component, as its polarization plane is first aligned with the polarization plane of one and then the other. The intensity of the unpolarized component of the light will undergo a constant attenuation of 50%, caused in a well-known manner by the randomness of the vibration planes of the unpolarized light. Some synchronization means, well within the capacity of the skilled practitioner, must be included so that the output signal representing the horizontal polarization intensity may be separated from that representing the vertical polarization intensity.

Referring again to the preferred embodiment illustrated in FIG. 1 of the drawing, one of the beams is transmitted through the horizontal polarization analyzer 40H. This will cause horizontally polarized light from the glitter pattern to pass through the analyzer unimpeded, while vertically polarized light is blocked, and unpolarized light is attenuated by 50%. The transmitted beam continues to a horizontal intensity detector 50H comprising, preferably, an ordinary silicon photodiode.

The other beam passes through the vertical analyzer 40V whose polarization plane is aligned in perpendicular orientation with respect to that of the first analyzer 40H. The second analyzer will pass unimpeded vertically polarized light, while horizontaly polarized light will be blocked, and unpolarized light will be attenuated in intensity by 50%. The transmitted beam is focused onto the vertical intensity detector 50V, also comprising a silicon photodiode.

Figure 2:
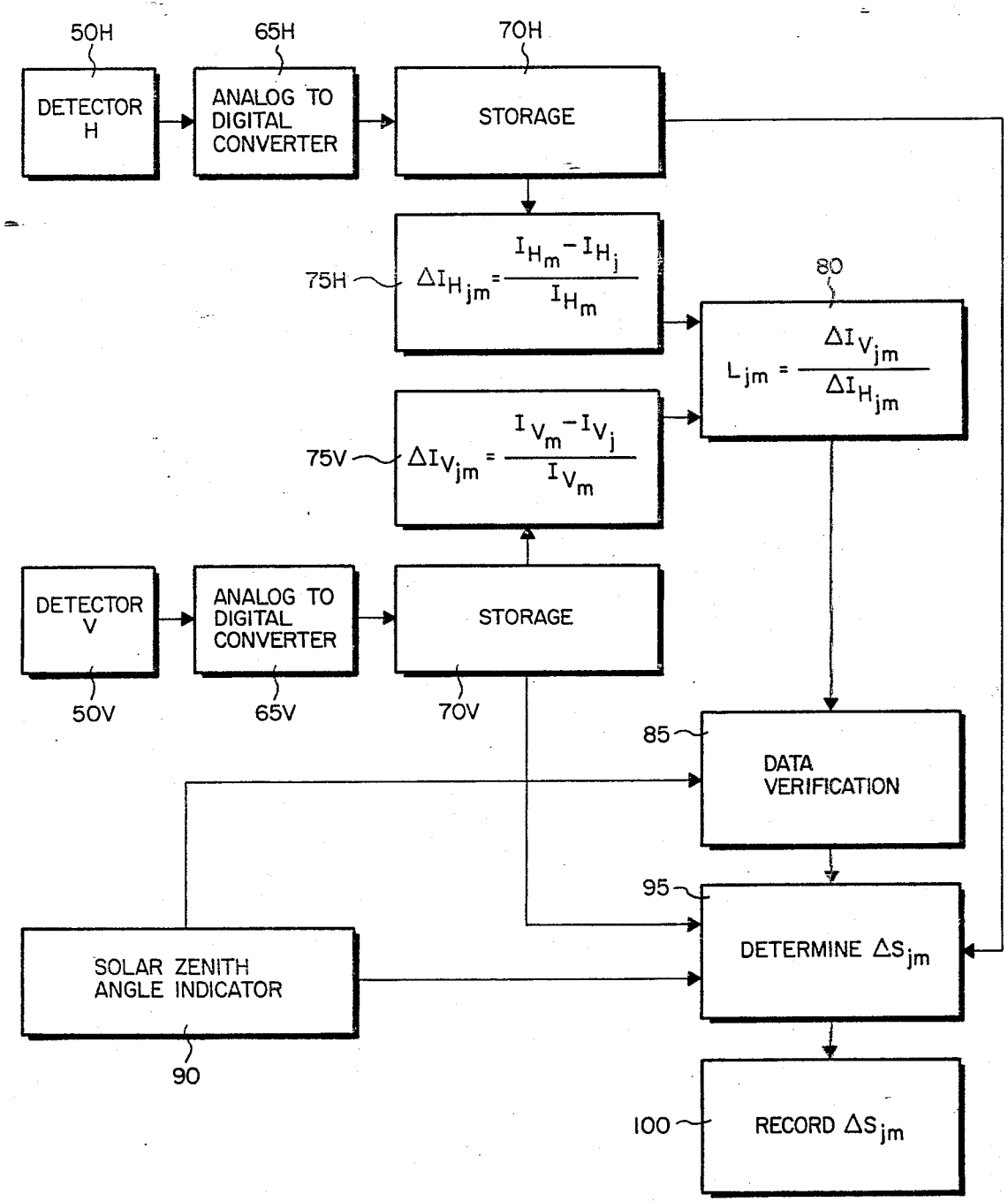
FIG. 2 is a logic block diagram of the steps in the computational portion of the preferred embodiment of the method of the invention.

Referring to FIG. 2, the output from the horizontal intensity detector 50H is fed into a conventional analog-to-digital converter 65H. The sampling rate of the analog to digital converter may be set as desired. Typically, a measurement sequence will obtain a total (M) in the order of 10,000 data. Thus, for a typical 100-second sequence, the frequency would be set at 100 data per second.

The output from the analog to digital converter 65H is fed to a storage means 70H which comprises a series of computer core locations, a magnetic tape, a disc file or similar "one dimensional" means for storing a series of values each representing the detected intensity of the horizontal component of polarized light reflected from the solar glitter pattern during a single intensity measurement.

Similarly, the other analog-to-digital converter 65V causes the storage means 70V to preserve a corresponding series of values each representing the detected intensity of the vertical component.

Thus, taken together, storage means 70H and storage means 70V will ultimately contain M data pairs, each data pair representing a value representing the detected intensity of the horizontally polarized component of light during a single solar glitter pattern measurement and a corresponding value for the vertically polarized component during the same measurement.

A given $jm^{th}$ data set, i.e., an $m^{th}$ (current) data pair together with a $j^{th}$ (previous) data pair, is operated on according to the following steps:

1. The storage means 70H outputs the $j^{th}$ and $m^{th}$ intensity values of the horizontally polarized component to the computational means 75H which computes the fractional change on intensity of the horizontally polarized component between the $j^{th}$ and $m^{th}$ measurement:

$$\Delta I_{H_{jm}} = \frac{I_{H_m} - I_{H_j}}{I_{H_m}}$$

2. Likewise, the storage means 70V outputs the corresponding $j^{th}$ and $m^{th}$ values of the intensity of the vertically polarized component into computational means 75V which calculates the corresponding fractional intensity change of the vertically polarized component according to the relationship:

$$\Delta I_{V_{jm}} = \frac{I_{V_m} - I_{V_j}}{I_{V_m}}$$

3. Computational means 80 receives the value computed in step 1 and the value computed in step 2 and computes their ratio, the empirical reference factor, according to the relationship:

$$L_{jm} = \frac{\Delta I_{V_{jm}}}{\Delta I_{H_{jm}}}$$

4. From the computed value of the empirical reference factor, $L_{jm}$, and the solar zenith angle, $\phi$, (which, it is assumed, has not changed materially during the entire measurement sequence), data verification means 85 determines whether the values represented by the $jm^{th}$ data set may be used to reliably compute the change in salinity between the point on the water surface representing the $j^{th}$ measurement and the point representing the $m^{th}$ measurement. Specifically, the data verification means determines whether the empirical reference factor, $L_{jm}$, satisfies either CONDITION A or CONDITION B, described above. This is done by:
a. Determining within which of the accepted ranges the solar zenith angle, $\phi$, falls, i.e., which of the two conditions might possibly be satisfied; and,
b. Determining, by comparison of the computer empirical reference factor with the criteria given above, whether the particular condition is, in fact, satisfied. The solar zenith angle indicator 90 is any means for outputting a signal corresponding to the solar zenith angle existing at the time the measurement of intensity were made. It is normally assumed that the solar zenith angle will not change materially during the entire measurement sequence, which will typically occupy a span in the order of 10 minutes. Thus, while the indicator might comprise a relatively complex device, such as a tracking detector in conjunction with a resolver and means for ascertaining the instantaneous orientation of the "down" vector, much simpler means may ordinarily be employed. Among these are a conventional clocking device to register the instantaneous date and time of day in conjunction with a stored (e.g., in a computer memory) file of solar zenith angles values for all dates and times, or a 365-day, 24-hour clock, which is adapted output the solar zenith angle rather than the time of day and date. Since the particular implementation of the solar zenith angle indicator chosen is not critical to the present invention, and since acceptable indication means will undoubtedly be withing the skill of the ordinary practitioner, the indicator need not be described in detail.

5. Based on the results of data verification by the data verification means 85, the computation means 95 either assigns a null value to the change in salinity, $\Delta S_{jm}$, between points on the water surface representing the $j^{th}$ and $m^{th}$ measurements, respectively, or actually calculates a value of $\Delta S_{jm}$. If a null value is to be assigned, i.e., if neither CONDITION A nor CONDITION B is satisfied by the $jm^{th}$ data set, the null value may actually be entered as a zero value in the memory location assigned to $\Delta S_{jm}$. However, since, in the usual case, at least 90% of the data sets obtained will result in null values, storage may be conserved by assigning no value whatever to $\Delta S_{jm}$ in such a case, and, if it is determined that a reliable value of $\Delta S_{jm}$ will be obtained, the actual value by calculating and recording, together with the integer values of $j$ and $m$. If CONDITION A or CONDITION B exists for the $jm^{th}$ data set, $\Delta S_{jm}$ is calculated as follows:
a. The refraction angles, $r$, for the $j^{th}$ and $m^{th}$ measurements are calculated by solving for $r$ in equation (3), in which $R_H$ is assumed to equal $K_R I_H$, where $K_R$ is the transfer function of the optical device (which is calculated, in a straightforward manner, by laboratory measurement of the detector outputs resulting from a known intensity input), and it is assumed that the incidence angle, $i$, is to equal $\phi$, the solar zenith angle.
b. Using the calculated values of $r$ and $r_m$, $n$, and $n_m$ are calculated from equation (4);
c. Using the latter values, $S_j$ and $S_m$ are calculated from equation (2); and
d. $S_j$ is subtracted from $S_m$ to yield $\Delta S_{jm}$, the salinity change between the $j^{th}$ and $m^{th}$ measurement points.

6. The value of $\Delta S_{jm}$ is then recorded in recording means 100, which may comprise a magnetic tape, disc file, computer core, battery of shift registers or other digital data storage means familiar to those skilled in the computer art. Suitable means well within the capability of the skilled practitioner may be included for extraction of the accumulated data from the recording means for subsequent display or analysis as desired. Again, there are two basic ways in which $\Delta S_{jm}$ may be recorded —
a. A value may be recorded representing each $jm^{th}$ data set (zero, if neither CONDITION A nor CONDITION B prevails or an actual value if a reliable value may be calculated), or
b. A representation of the calculated $\Delta S_{jm}$ value may be recorded together with the integral values of $j$ and $m$, only where data verification means 85 has shown that the calculated value will be reliable.

Both data storage formats are entirely familiar to those skilled in the computer art.

Following the foregoing six operations with the $jm^{th}$ data set, these operations are repeated with the "next" data set. Typically, the next set will be the $(m+1)m^{th}$ set, i.e., the "current" ($m^{th}$) data pair and the next most proximate $(j+1)^{th}$ previous data pair. The next data set could, of course, be the $j(m+1)^{th}$ data set or any other for that matter. However, as indicated, it is preferable that the current ($m^{th}$) value be fixed while the index representing the previous values ($j$) is incremented as the six steps are repeated in cyclic fashion.

When the "previous value" index ($j$) has been incremented through the entire desired range, the "current value index" ($m$) is then incremented by one and the $j$ index is again incremented throughout the entire selected range, each data set representing a specific $jm$ combination being operated on according to the foregoing six steps.

From the foregoing it might appear reasonable to assume that each "current value" data pair is compared with each "previous value" data pair. I.e., for each $m$ index the $j$ index is incremented from 1 to $m-1$, so that there will be $m-1$ data sets, each operated on according to the foregoing six steps.

While such a scheme might be practical if the total number, M, of measurements were held to a rather small value, such will typically not be the case. Ordinarily M will be in the order of 10,000. This being the case, it can readily be seen that if, for each current ($m^{th}$) measurement, a comparison must be made with each previous ($j^{th}$) measurement and there are 10,000 measurements in all, steps 1 to 6, above, will have to be performed approximately $5 \times 10^7$ times. Besides being wasteful of computer time, such a scheme would probably result in the generation of a large amount of redundant or otherwise useless data.

Accordingly, it is preferred that each current ($m^{th}$) data pair be compared with only a limited number, $x$ (for example 100), of the most proximate previous ($j^{th}$) data pairs. Thus, for each $m$, $j$ would be incremented from some initial value $j$ to $m-1$.

Initially, for each value of $m$, $j$ is incremented from 1 to $m-1$. When $m = x+1$ or more, $j$ is incremented from $m-x$ to $m-1$. This continues until $m = M$ (corresponding to the last measurement) and $m = M-1$ (the measurement just prior to the last measurement). This is the final data set.

Summarizing the foregoing, it can be seen that the typical sequence of data sets, each of which is operated on according to the six foregoing steps, is as follows:

| | |
|---|---|
| $m = 2$, | $j = 1$ |
| $m = 3$, | $j = 1$ |
| $m = 3$, | $j = 2$ |
| $m = 4$, | $j = 1$ |
| $m = 4$, | $j = 2$ |
| . | |
| $m = 200$, | $j = 197$ |
| $m = 200$, | $j = 198$ |
| $m = 200$, | $j = 199$ |
| $m = 201$, | $j = m-x$ |
| $m = 201$, | $j = m-x+1$ |
| $m = 201$, | $j = m-x+2$ |
| . | |
| $m = 201$, | $j = 200$ |
| $m = 202$, | $j = m-x$ |
| . | |
| $m = M-1$, | $j = M-3$ |
| $m = M-1$, | $j = M-2$ |
| $m = M$, | $j = M-x$ |
| $m = M$, | $j = M-x+1$ |
| . | |
| $m = M$, | $j = M-2$ |
| $m = M$, | $j = M-1$ |

The final result of operating on all specified data sets according to the foregoing operations is a series of values each representing a change in salinity $\Delta S_{jm}$ between pairs of points on the surface of the body of water under investigation. As previously stated, these values may be represented logically as a two-dimensional matrix, each position in the matrix being represented by a $\Delta S_{jm}$ value, if data verification has shown that a reliable value may be calculated, or a null value, if a reliable value may not be calculated. Alternatively, the data may be represented one-dimensionally as a sequence of $\Delta S_{jm}$ values together with a respective values of the $j$ and $m$ indices, with no entry whatever representing those $jm$ data pairs for which a reliable value of $\Delta S_{jm}$ may not be computed.

Comparison of each salinity change value with an initial "truth" reading of local salinity will permit calculation of the actual salinity at a large number of points along the path traversed by the salinity sensing apparatus of the present invention. These may be represented in tabular form and/or may be transferred to a map of the region of the body of water being surveyed to graphically represent salinity contours.

The means for accomplishing the foregoing operational steps comprises, in the preferred embodiment of the invention, a programmed general purpose digital computer. The actual program utilized by the practitioner is not critical to the operation of the invention, although it is preferred that the logical sequence of steps performed be those shown in the flow chart illustrated in FIG. 3 of the drawing wherein each preferred logical step is represented by a universally recognized logic symbol.

Figure 3A:
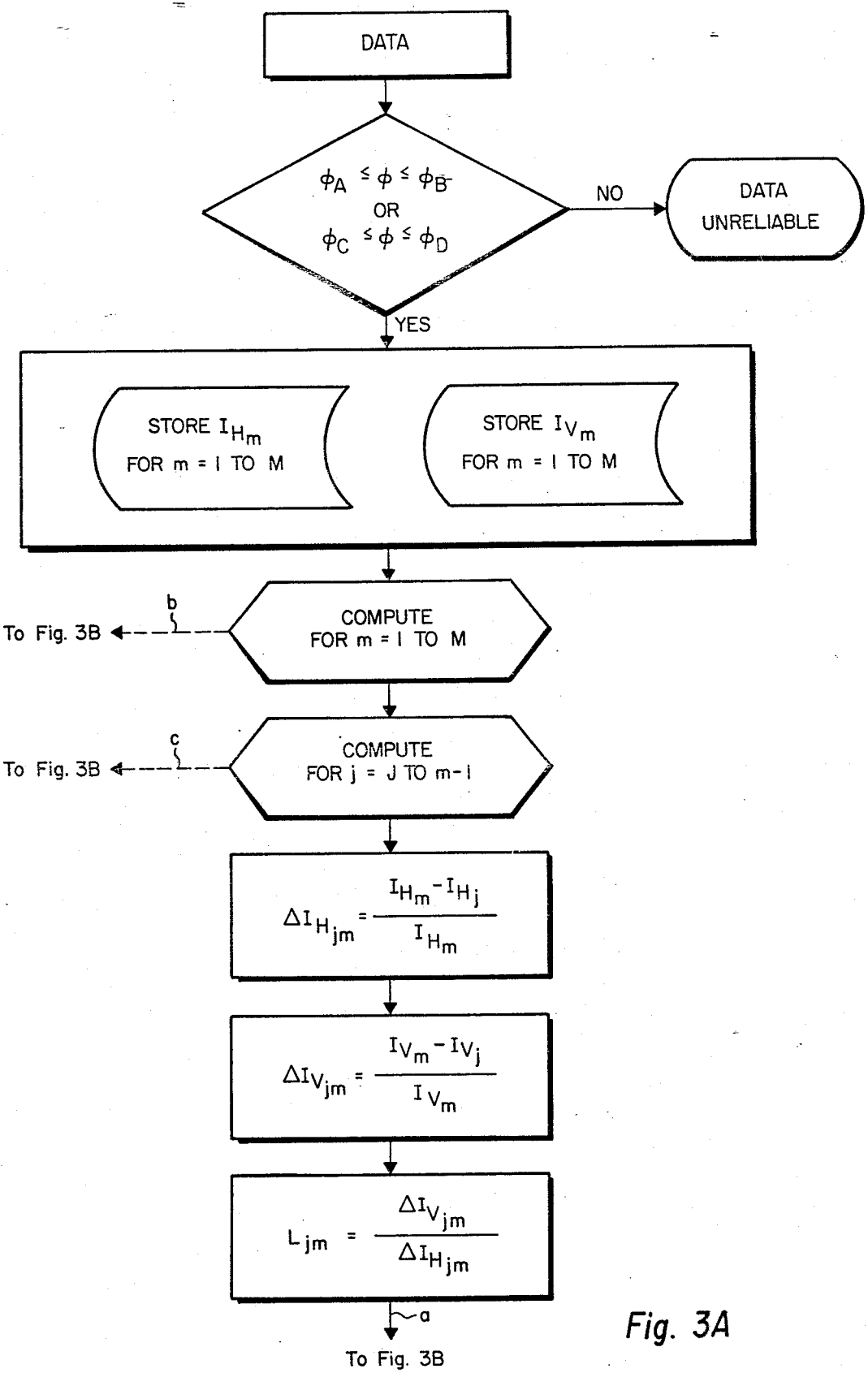
FIGS. 3A and 3B are, together, a flow chart showing, in detail, a number of steps of the sequence shown in FIG. 2.
Figure 3B:
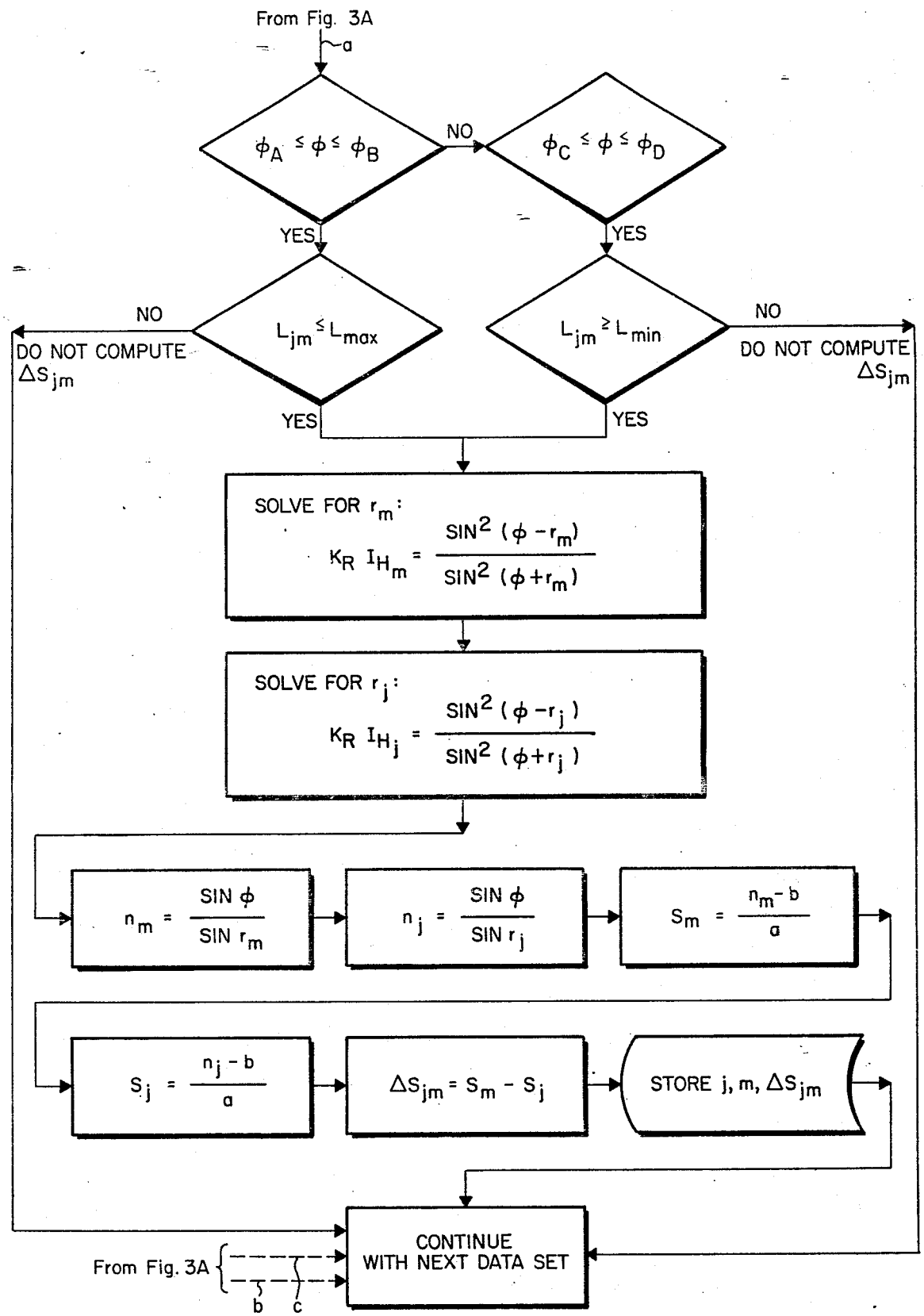

The logic flow chart shown in FIG. 3 may also be readily used by a reasonably skilled logic design engineer to produce "hard-wired" embodiment of the computational means.

The axis (axes, in the illustrated preferred embodiment) of the optical sensor of the present invention must always be pointed, with reasonable accuracy, at the center of the glitter pattern, so that true specular reflection readings may be obtained. This requires that some sort of sensor pointing apparatus be employed. While numerous means could be employed, a workable apparatus is shown schematically in FIG. 6.

Here, an array of four photodetectors is arranged in quadrants numbered A, B, C and D. Optical means not shown causes a light beam from the solar glitter pattern on the ocean surface to be focused onto the array. This light beam is parallel to the beam received by the primary optical sensor apparatus. This can, of course, be accomplished by rigid parallel mounting of the optical sensor and the pointer.

Figure 6:
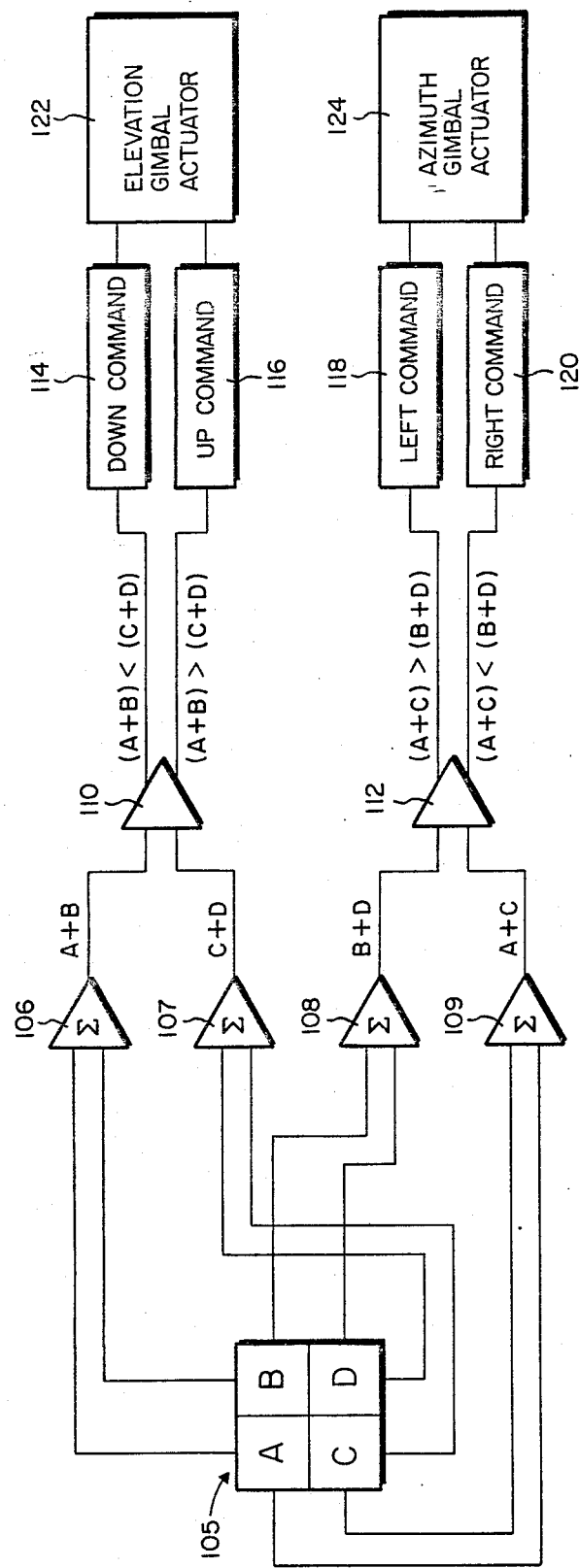
FIG. 6 is a schematic representation of the preferred apparatus utilized in directing the sensor of the present invention for solar glitter pattern tracking.

In order for convenience in describing the operation of the detector array 105, one must view the array shown schematically in FIG. 6 as if the viewer were behind the array looking toward the glitter pattern on the opposite side.

Assuming each of the detectors is calibrated so that light of a given intensity impinging on any of them will generate the identical output signal amplitude, it follows that if the signal amplitude for each of the detectors is identical, the intensity of light detected by each is identical. Thus, if an image of a remote light source is focused onto the detector array 105 in such a manner that the output signal amplitude from detectors A, B, C and D is identical, it may be safely assumed that if the light source subtends a relatively small angle at the sensor, the sensor is locked onto the center of the light source. If this were not the case, at least one of the detectors would generate a lower output signal amplitude since it would be viewing an edge of the pattern or a region outside the pattern while at least one of the others would be more wholly saturated by light from within the pattern.

Specifically, if the output from detectors A and B together is greater than that from C and D, the detector array 105 is pointed too low, i.e., the image focuses onto the upper detectors comes from a region more wholly within the remote light pattern than that focused onto the lower detectors which originate in the region below the pattern. The indicated corrective action would be to tilt the sensor slightly upward so that the lower detectors receive as much light as the upper detectors.

Likewise, if the left detectors A and C receive more light than the right detectors, B and D, the sensor is aimed too far to the right of the remote light source being sensed, and the corrective action would be to tilt the sensor somewhat to the left until both sides receive the same amount of light.

Thus, a remote light pattern can be tracked simply by insuring that detectors A and B receive the same amount of light as detector C and D (for vertical control) and that detectors A and C receive as much light as detectors B and D (for horizontal control).

Accordingly, the tracking sensor of the present invention comprises optical means for imaging the remote light source onto the detector array 105 and gimbal actuator means operating in response to the output of the detectors A, B, C and D of the array in such a manner that the housing for the tracking sensor (ordinarily a satellite or a portion of it) may be continuously oriented so that the image is centered within the detector array.

To accomplish vertical stabilization, the outputs from detectors, A and B are summed by a summing amplifier 106, and the outputs from detectors C and D are summed by another summing amplifier 107. The outputs from the two summing amplifiers are fed into a comparator 110 which determines whether the sum of the outputs from detectors A and B is greater or less than the sum of the outputs from detectors C and D. If the sum from A and B is less than the sum from C and D, this indicates that the tracking sensor is aimed too high, and a down-command means 114 is actuated to generate an appropriate command to the elevation gimbal actuator 122 for corrective action in orienting the tracking sensor housing.

Horizontal corrections are made by causing the outputs of detectors B and D to be summed by a summing amplifier 108, and the output from detectors A and C to be summed by another summing amplifier 109. A comparator 112 determines whether the sum from A and C is greater or less than the sum from B and D. If it is greater, the tracking sensor is tilted too far to the right of the remote source, and a corrective left command to the azimuth gimbal actuator 124 is generated by the left command means 118. On the other hand, if the sum from A and C is less than the sum from B and D, the azimuth gimbal actuator is commanded by the right command means 120.

Of course, means must be provided to insure that the image of the remote light pattern is focused somewhere within the detector array 105. There are a number of ways of accomplishing this which are familiar to those skilled in the satellite navigation art. One is, of course, to provide an optical apparatus with a field of view of sufficient width to encompass the entire solar glitter pattern and some of the surrounding territory.

I claim:

1. In a method of remotely determining the degree of salinity of water at a specified point at the surface of a body thereof, the steps of:
   a. electro-optically generating a first data signal representative of a first value, corresponding to the intensity of at least a finite wavelength band of the horizontally-polarized component of sunlight specularly reflected from a solar glitter pattern at the specified point;
   b. electro-optically generating a second data signal representative of a second value, corresponding to the intensity of at least a finite wavelength band of the horizontally-polarized component of sunlight specularly reflected from the solar glitter pattern at another point;
   c. electro-optically generating a third data signal representative of a third value, corresponding to the intensity of at least a finite wavelength band of the vertically polarized component of sunlight specularly reflected from the solar glitter pattern at the specified point;
   d. electro-optically generating a fourth data signal representative of a fourth value, corresponding to the intensity of at least a finite wavelength band of the vertically polarized component of sunlight specularly reflected from the solar glitter pattern at the other point;
   e. electronically operating on said first data signal and said second data signal to compute a first difference between the first value and the second value;
   f. electronically operating on said third data signal and said fourth data signal to compute a second difference between the third value and the fourth value;
   g. electronically computing a first ratio of said first difference to said first value;
   h. electronically computing a second ratio of said second difference to said third value; and
   i. electronically computing an empirical reference factor, defined as the ratio of said second ratio to said first ratio.

2. The method as recited in claim 1, wherein said steps of generating each comprise the steps of:
   a. optically receiving light projected from the glitter pattern;
   b. causing at least a finite wavelength band of the received light to impinge on detector means adapted to generate an electrical signal whose instantaneous amplitude represents the instantaneous intensity of the impinging light; and
   c. converting said electrical signal to said data signal.

3. The method as recited in claim 2, wherein each of said electrical signals is an analog signal, each of said data signals is a digital signal and said steps of converting each comprise converting said analog signal to said digital signal.

4. In an apparatus for remotely determining the degree of salinity of water at a specified point at the surface of a body thereof, the combination comprising:
   a. first electro-optical means for generating a first data signal and a second data signal, the first data signal representative of a first value, corresponding to the intensity of at least a finite wavelength band of the horizontally polarized component of sunlight specularly reflected from a solar glitter pattern at the specified point, and the second data signal representative of a second value, corresponding to the intensity of at least a finite wavelength of the horizontally polarized component of sunlight specularly reflected from the solar glitter pattern at another point;
   b. second electro-optical means for generating a third data signal and a fourth data signal, the third data signal representative of a third value, corresponding to the intensity of at least a finite wavelength band of the vertically polarized component of sunlight specularly reflected from the solar glitter pattern at the specified point, the fourth data signal representative of a fourth value, corresponding to the intensity of at least a finite wavelength band of the vertically polarized component of sunlight specularly reflected from the solar glitter pattern at the other point;

c. electronic means for operating on said first data signal and said second data signal to compute a first difference between the first value and the second value;

d. electronic means for operating on said third data signal and said fourth data signal to compute a second difference between the third value and the fourth value;

e. electronic means for computing a first ratio of the first difference to the first value;

f. electronic means for computing a second ratio of the second difference to the third value; and g. electronic means for computing an empirical reference factor, defined as the ratio of the second ratio to the first ratio.

5. The apparatus as recited in claim 4 wherein:

said first electro-optical means comprises detector means adapted to generate an electrical signal whose instantaneous amplitude represents the instantaneous intensity of at least a finite wavelength band of light impinging thereon, optical means to receive light radiated from the glitter pattern and to cause at least the finite wavelength band thereof to impinge on said detector means, and polarizing means intervening between said detector means and said optical means, said polarizing means adapted to pass, substantially unimpeded, the horizontally polarized component of the light radiated from the glitter pattern and to substantially block the vertically polarized component of the light radiated therefrom; and said second electro-optical means comprises detector means adapted to generate an electrical signal whose instantaneous amplitude represents the instantaneous intensity of at least a finite wavelength band of light impinging thereon, optical means to receive light radiated from the glitter pattern and to cause at least the finite wavelength band thereof to impinge on said detector means, and polarizing means intervening between said detector means and said optical means, said polarizing means adapted to pass, substantially unimpeded, the vertically polarized component of the light radiated from the glitter pattern and to substantially block the horizontally polarized component of the light radiated therefrom.

6. The apparatus as recited in claim 5 further including means to convert each of the electrical signals to a corresponding data signal.

7. The apparatus as recited in claim 6 wherein each of the electrical signals comprises an analog signal, each of the data signals comprises a digital signal, and said conversion means comprises electronic analog-to-digital conversion means.

8. The apparatus as recited in claim 5 further including:

first optical filtering means adapted to pass only a finite wavelength band of light impinging thereon, said first optical filtering means interposed between said first detector means and the glitter pattern; and second optical filtering means adapted to pass substantially the same wavelength band as said first optical filtering means, said second optical filtering means interposed between said second detector means and the glitter pattern.

9. The apparatus as recited in claim 5 further including:

first neutral filtering means adapted to non-selectively reduce the intensity of the light impinging upon said first detector means; and second neutral filtering means adapted to nonselectively reduce the intensity of the light impinging upon said second detector means.

10. The apparatus as recited in claim 4 further including tracking sensor means operably connected to said first electro-optical means and said second electro-optical means, said tracking sensor means adapted to cause said first electro-optical means and said second electro-optical means to be oriented with respect to the solar glitter pattern in such a manner that the intensity of the light impinging upon said first and second electro-optical means is substantially maximized.

11. The apparatus as recited in claim 10 wherein said tracking sensor means comprises:

electro-optical detector means oriented with respect to the glitter pattern in such a manner as to receive a beam of light reflected therefrom, said detector means adapted to generate a first electrical tracking signal whose instantaneous amplitude is representative of the instantaneous intensity of the upper portion of the beam, a second electrical tracking signal whose instantaneous amplitude is representative of the instantaneous intensity of the lower portion of the beam, a third electrical tracking signal whose instantaneous amplitude is representative of the instantaneous intensity of the leftward portion of the beam, and a fourth electrical tracking signal whose instantaneous amplitude is representative of the instantaneous intensity of the rightward portion of the beam;

electronic means to compare the amplitudes of said first and second electrical signals and to compare the amplitudes of said third and fourth electrical signals, said electronic comparison means adapted to determine by what amount the angular orientation of said detector means must be altered in order to cause the amplitude of said first signal to equal that of said second signal and the amplitude of said third signal to equal that of said fourth signal, and, based on this determination, to generate an electrical command signal representative of said reorientation data; and electro-mechanical means responsive to said reorientation command signal adapted, in response thereto, to reorient said tracking sensor means so that the amplitude of said first electrical signals equals the amplitude of said second electrical signal and the amplitude of said third electrical signal equals the amplitude of said fourth electrical signal, said reorientation means adapted also to reorient said first electro-optical means and said second electro-optical means in such manner that upon reorientation of said tracking sensor detector means, the intensity of light impinging on said first electro-optical means and upon said second electro-optical means is substantially maximized.

12. The apparatus as recited in claim 11, wherein said first electro-optical means, said second electro-optical means and said electro-optical detector are mutually mechanically connected in substantially rigid manner.

13. In an apparatus for remotely determining the degree of salinity of water at a specified point at the surface of a body thereof, the combination comprising:
   a. electro-optical means for generating a first data signal, a second data signal, a third data signal and a fourth data signal, the first data signal representative of a first value, corresponding to the intensity of at least a finite wavelength band of the horizontally polarized component of sunlight specularly reflected from a solar glitter pattern at the specified point, the second data signal representative of a second value, corresponding to the intensity of at least a finite wavelength band of the horizontally polarized component of sunlight specularly reflected from the solar glitter pattern at another point, the third data signal representative of a third value, corresponding to the intensity of at least a finite wavelength band of the vertically polarized component of sunlight specularly reflected from the solar glitter pattern at the specified point, and the fourth data signal representative of a fourth value, corresponding to the intensity of at least a finite wavelength band of the vertically polarized component of sunlight specularly reflected from the solar glitter pattern at the other point;
   b. electronic means for operating on said first data signal and said second data signal to compute a first difference between the first value and the second value;
   c. electronic means for operating on said third data signal and said fourth data signal to compute a second difference between the third value and the fourth value;
   d. electronic means for computing a first ratio of the first difference to the first value;
   e. electronic means for computing a second ratio of the second difference to the third value; and
   f. electronic means for computing an empirical reference factor, defined as the ratio of the second ratio to the first ratio.

14. The appaaratus as recited in claim 13 wherein said electro-optical means comprises:
   detector means adapted to generate an electrical signal whose instantaneous amplitude represents the instantaneous intensity of at least a finite wavelength band of light impinging thereon;
   optical means to receive a light radiated from the glitter pattern and to cause at least the finite wavelength band thereof to impinge on said detector means;
   polarizing means intervening between said detector means and said optical means, said polarizing means adapted to pass, substantially unimpeded, the plane polarized component of the light radiated from the glitter pattern whose polarization plane is aligned with the polarization plane of the polarizing means and to substantially block the plane polarized light whose polarization plane is opposed to that of said polarizing means, said polarizing means adapted to selectively cause the orientation of the polarization plane thereof to change.

15. The apparatus as recited in claim 14 wherein said polarizing means comprises a rotating polarizer and means to cause selective rotation thereof.

16. The apparatus as recited in claim 14 wherein each of the electrical signals comprises an analog signal, each of the data signals comprises a digital signal, and further including electronic analog-to-digital conversion means to convert each of the electrical signals to a corresponding data signal.

17. The apparatus as recited in claim 14 further including optical filtering means adapted to pass only a finite wavelength band of light impinging thereon, said optical filtering means interposed between said detector means and the glitter pattern.

18. The apparatus as recited in claim 14 further including neutral filtering means adapted to non-selectively reduce the intensity of the light impinging on said detector means.

19. The apparatus as recited in claim 13 further including tracking sensor means operably connected to said electro-optical means, said tracking sensor means adapted to cause said electro-optical means to be oriented with respect to the solar glitter pattern in such a manner that the intensity of the light impinging upon said electro-optical means is substantially maximized.

20. The apparatus as recited in claim 19 wherein said tracking sensor means comprises:
   electro-optical detector means oriented with respect to the glitter pattern in such a manner as to receive a beam of light reflected therefrom, said detector means adapted to generate a first electrical tracking signal whose instantaneous amplitude is representative of the instantaneous intensity of the upper portion of the beam, a second electrical tracking signal whose instantaneous amplitue is representative of the instantaneous intensity of the lower portion of the beam, a third electrical tracking signal whose instantaneous amplitude is representative of the instantaneous intensity of the leftward portion of the beam, and a fourth electrical tracking signal whose instantaneous amplitude is representative of the instantaneous intensity of the rightward portion of the beam;
   electronic means to compare the amplitudes of said first and second electrical signals and to compare the amplitudes of said third and fourth electrical signals, said electronic comparison means adapted to determine by what amount the angular orientation of said detector means must be altered in order to cause the amplitude of said first signal to equal that of said second signal and the amplitude of said third signal to equal that of said fourth signal, and, based on this determination, to generate an electrical command signal representative of said reorientation data; and
   electro-mechanical means responsive to said reorientation command signal adapted, in response thereto, to reorient said tracking sensor means so that the amplitude of said first electrical signal equals the amplitude of said second electrical signal and the amplitude of said third electrical signal equals the amplitude of said fourth electrical signal, said reorientation means adapted also to reorient said electro-optical means in such manner that upon reorientation of said tracking sensor detector means, the intensity of light impinging on said electro-optical means, is substantially maximized.

21. The apparatus as recited in claim 20, wherein said electro-optical means and said electro-optical detector are mutually mechanically connected in a substantially rigid manner.

* * * * *